United States Patent [19]

Griggs et al.

[11] Patent Number: 4,609,763

[45] Date of Patent: Sep. 2, 1986

[54] PROCESS FOR THE OXIDATION OF HYDROCARBONS

[75] Inventors: Colin G. Griggs, Ashford; Anthony R. Middleton, Staines, both of England

[73] Assignee: The British Petroleum Company P.L.C., London, England

[21] Appl. No.: 771,987

[22] Filed: Sep. 3, 1985

[30] Foreign Application Priority Data

Sep. 5, 1984 [GB] United Kingdom ............... 8422443

[51] Int. Cl.$^4$ ............................................. C07C 45/30
[52] U.S. Cl. ................................... 568/342; 568/385; 568/836; 568/910
[58] Field of Search ............... 568/342, 385, 836, 910

[56] References Cited

U.S. PATENT DOCUMENTS

| | | | |
|---|---|---|---|
| 3,114,773 | 12/1963 | Brill ..................................... | 568/385 |
| 3,231,620 | 1/1966 | Cotterill et al. ..................... | 568/342 |
| 3,337,635 | 8/1967 | Norton et al. ....................... | 568/385 |
| 3,518,285 | 6/1970 | Fenton et al. ....................... | 568/385 |
| 3,879,467 | 4/1975 | Zajacek et al. ...................... | 568/836 |
| 3,925,316 | 12/1975 | Brunie et al. ........................ | 568/342 |
| 3,948,992 | 4/1976 | McMahon ........................... | 568/342 |
| 4,459,427 | 7/1984 | Middleton et al. .................. | 568/836 |
| 4,480,135 | 10/1984 | Esposito et al. .................... | 568/342 |

*Primary Examiner*—James H. Reamer
*Attorney, Agent, or Firm*—Brooks, Haidt, Haffner & Delahunty

[57] ABSTRACT

A process for the oxidation of alkanes or alkenes is described. The process uses a hydrocarbyl hydroperoxide as an oxidizing agent in combination with a ruthenium catalyst and optionally a hydrogen bromide or hydrobromide acid promoter. The products of the oxidation are alcohols, ketones or a mixture of both.

8 Claims, No Drawings

PROCESS FOR THE OXIDATION OF HYDROCARBONS

This invention relates to a process for the oxidation of hydrocarbons and in particular to the oxidation of alkanes or alkenes having from 3 to 20 carbon atoms to produce the corresponding alcohol or ketone using a hydrocarbyl hydroperoxide as the oxidising agent.

The oxidation of hydrocarbons to alcohols or ketones using hydroperoxides has been described previously. Thus, U.S. Pat. No. 3,879,467 claims such a method of oxidising hydrocarbons using a chromium catalyst.

Our corresponding European patent application No. 0,079,705 also describes a process by which hydrocarbons are oxidised to alcohols and ketones using a hydrocarbyl hydroperoxide. However in this application the catalyst is iron and in the form of a metalloporphyrin.

It has now been discovered that the oxidation of hydrocarbons to alcohols and ketones using a hydrocarbyl hydroperoxide can be catalysed by a soluble ruthenium compound.

Accordingly, the present invention provides a process for the oxidation of alkanes or alkenes to produce an alcohol, ketone or mixture thereof, which process comprises reacting an alkane or an alkene with a hydrocarbyl hydroperoxide in the liquid phase characterised in that the reaction is carried out in the presence of an effective amount of a soluble ruthenium catalyst.

The alkane or alkene feedstock which is used is conveniently one having from 3 to 20 carbon atoms and is preferably one having from 5 to 10 carbon atoms. If the feedstock is an alkane it can be linear, for example n-butane, cyclic, for example cyclohexane, or branched, for example 2,3-dimethylbutane, 2-methylhexane and the like. If an alkene is used as feedstock it it preferable that it has only one double bond per molecule. In addition mixtures of alkanes and/or alkenes can be used.

As regards the hydrocarbyl hydroperoxide, this is suitably an alkyl, cycloalkyl or aryl hydroperoxide. Hydroperoxides containing both alkyl and aryl groups can also be used. Preferred hydrocarbyl hydroperoxides include t-butylhydroperoxide, cumene hydroperoxide and cyclohexylhydroperoxide. The hydrocarbyl hydroperoxide may be added to the reaction medium undiluted or as a solution in an inert solvent.

The stoichiometry of the reaction requires that for every mole of alcohol produced from the hydrocarbon 1 mole of hydrocarbyl hydroperoxide is consumed while for every mole of ketone produced 2 moles of hydrocarbyl hydroperoxide are consumed. However, as the hydrocarbyl hydroperoxide is the more expensive feedstock it is often preferable to operate the process in the presence of excess alkane or alkene. Under these conditions it is still possible to produce both alcohol and ketone. Suitably, the molar ratio of alkane or alkene to hydrocarbyl hydroperoxide should be in the range from 10:1 to 1:10 preferably from 5:1 to 1:2.

The alcohol or ketone produced during the reaction is that derived from the alkane or alkene. Thus, if cyclohexane is used as the alkane, the product is cyclohexanol, cyclohexanone or a mixture thereof. In addition to these products there may also be present at the end of the reaction detectable quantities of (1) the alcohol and other products produced by thermal decomposition of the hydrocarbyl hydroperoxide and (2) hydroperoxides or peroxides produced by reaction of radicals formed in the process e.g. tertiarybutylcyclohexyl peroxide if tertiarybutyl hydroperoxide is used as the oxidant.

Any soluble ruthenium compound can be used as catalyst. Thus a halide such as ruthenium trichloride, an inorganic complex such as a ruthenium(dimethylglyoximato)diphosphine and a ruthenium dihalodiphosphine e.g. $RuCl_2(PPh_3)_2$, or an organic complex such as tris-(acetoacetonate)ruthenium (III) can be used. Ruthenium porphyrins and phthalocyanines are also suitable catalysts. The amount of catalyst added should be for preference less than 10,000 ppm by weight of the total reaction mixture.

The reaction can be carried out at ambient temperature, or at elevated temperatures. Preferably the reaction temperature should be in the range ambient temperature to 140° C., more preferably in the range 60°–120° C.

Although the reactants themselves can be used as solvent it is preferable to add an inert solvent, which does not undergo substantial oxidation under the reaction conditions, to the reaction mixture in order to increase the catalyst solubility, to moderate the reaction or as a medium for the introduction of the hydrocarbyl hydroperoxide. The solvent may be for example one which is miscible with the reactants, e.g. tertiary butanol, chlorobenzene toluene, acetic acid, acetone and pyridine. It is convenient to add the solvent in amounts equivalent to the volume of one of the two reactants.

When a ruthenium compound is used as a catalyst it is advantageous to add small amounts of aqueous hydrobromic acid or gaseous hydrogen bromide as a promoter in order to increase the efficiency of hydroperoxide usage.

Accordingly, an embodiment of the present invention provides a process for the oxidation of alkanes or alkenes to produce the corresponding alcohol or ketone, which process comprises reacting the alkane or alkene with a hydrocarbyl hydroperoxide in the liquid phase characterised in that the reaction is carried out in the presence of an effective amount of a soluble ruthenium catalyst and hydrobromic acid or hydrogen bromide.

The hydrobromic acid or hydrogen bromide is preferably added in an amount which is less than 2% by weight of the reactants.

The process may be carried out either batchwise or continuously.

The present invention will now be illustrated by the following Examples.

In all of the following Examples, catalyst turnover is defined as:

$$\text{Catalyst Turnover} = \frac{\text{mmol of TBHP converted to oxidised cyclohexane products}}{\text{mmol of catalyst added}}$$

EXAMPLES 1–7

A solution of cyclohexane (20 ml, 185 mmol), benzene (20 ml) and the appropriate catalyst (0.1 g) was prepared and degassed with nitrogen under reflux conditions, while being stirred magnetically. To this stirred cyohexane/benzene/catalyst solution was then added, dropwise, t-butyl hydroperoxide (TBHP) in t-butanol (20 ml, 2–4 M in hydroperoxide) over a period of 30 mins. The reaction was maintained at reflux, with stirring. During this time, the disappearance of hydroperoxide was monitored by GLC. Upon completion of the reaction, the products were quantitatively analysed by GLC using standard methods. Table 1 summarises the results obtained for a range of ruthenium catalysts.

TABLE 1
EFFECT OF CATALYST

| | | | | Mole % Product Distribution | | | |
|---|---|---|---|---|---|---|---|
| Example | Catalyst | % TBHP Consumed | % TBHP Selectivity | Cyclohex-anone | Cyclohex-anol | t-Butyl cyclohexyl-peroxide | Catalyst Turnover |
| 1 | Ru(acac)$_3$ | 100 | 63 | 35 | 17 | 48 | 124 |
| 2 | RuCl$_3$ | 100 | 59 | 35 | 34 | 31 | 121 |
| 3 | Ru(DMGH)$_2$(PPh$_3$)$_2$ | 100 | 58 | 39 | 31 | 30 | 322 |
| 4 | Ru$_3$O(OAc)$_6$(H$_2$O)$_3^+$OAc | 100 | 51 | 35 | 33 | 32 | 216 |
| 5 | Ru(TPP)(CO)(THF) | 100 | 44 | 47 | 33 | 20 | 387 |
| 6 | Ru(bipy)$_3^{2+}$2Cl$^-$ | 100 | 42 | 28 | 30 | 42 | 212 |
| 7 | Ru(bipy)$_2$Cl$_2$ | 100 | 41 | 36 | 43 | 31 | 134 |

DMGH = dimethylglyoximato
bipy = bipyridine
THF = tetrahydrofuran
OAC = acetate
TPP = tetraphenylporphyrinato
acac = acetoacetonato
PPh$_3$ = triphenylphosphine

EXAMPLES 8–14

A solution of cyclohexane (20 mls, 185 mmol) solvent (20 ml) and tris(acetylacetato) ruthenium (III) (0.0015 g) were degassed by reflux under nitrogen with stirring. To the stirred, refluxing cyclohexane/solvent/catalyst solution was then added, dropwise, t-butyl hydroperoxide in t-butanol (20 ml, 2–4M in hydroperoxide) over a period of 30 minutes. The reaction was maintained at reflux, with stirring, and the disappearance of the hydroperoxide monitored by GLC. Upon completion of the reaction the products were quantitatively analysed by GLC using standard methods.

The results are summarised in Table 2.

EXAMPLE 15

A solution of cyclohexane (20 ml, 185 mmol), benzene (20 ml), and ruthenium tris(acetoacetonate) catalyst (0.001 g–0.1 g) was degassed by reflux under nitrogen. Hydrobromic acid (4 drops of concentrated acid, specific gravity 1.5) was then added followed by a solution of t-butyl hydroperoxide in t-butanol (20 ml) of a 2–4 molar solution). The hydroperoxide solution was added dropwise over 30 minutes with the reaction maintained at reflux. As soon as the t-butyl hydroperoxide was consumed, the products were analysed by GLC. The results are given in Table 3.

EXAMPLE 16

Example 15 was repeated except that the hydrobromic acid was omitted. The results are shown in Table 3.

EXAMPLE 17

The method of Example 15 was followed except that 2 mg of sodium bromide were used in place of hydrobromic acid. The results are given in Table 3.

EXAMPLE 18 AND 19

In each test, the method of Example 15 was used except that the hydrobromic acid was replaced by either hydrochloric acid or hydroiodic acid. The results are given in Table 3.

EXAMPLE 20

To a solution of t-butyl hydroperoxide in t-butanol (20 ml, 4 molar in hydroperoxide) was added hydrobromic acid (4 drops of concentrated acid, SG 1.50). This solution was then added dropwise, over 30 mins, to a refluxing solution of cyclohexane (20 ml), solvent (20 ml) and a catalyst (0.001–0.1 g), which had been previously degassed under nitrogen. The reaction was main-

TABLE 2
EFFECT OF SOLVENT

| | | | | Mole % Product Distribution | | | |
|---|---|---|---|---|---|---|---|
| Example | Catalyst | % TBHP Consumed | % TBHP Selectivity | Cyclohex-anone | Cyclohex-anol | t-Butyl cyclohexyl-peroxide | Catalyst Turnover |
| 8 | t-BuOH | 100 | 59 | 43 | 22 | 35 | 13,200 |
| 9 | C$_6$H$_6$ | 100 | 51 | 40 | 27 | 33 | 11,400 |
| 10 | (CH$_3$)$_2$CO | 100 | 51 | 42 | 26 | 32 | 11,400 |
| 11 | — | 100 | 47 | 46 | 33 | 21 | 10,550 |
| 12 | isooctane | 100 | 41 | 39 | 35 | 26 | 9,200 |
| 13 | CH$_3$CO$_2$H | 91 | 61 | 33 | 25 | 42 | 11,050 |
| 14 | C$_5$H$_5$N | 53 | 46 | 65 | 17 | 18 | 8.480 | tained at reflux, with stirring, while monitoring the disappearance of hydroperoxide by glc. The products were quantitatively analysed by glc upon completion of the reaction.

Examples 15 and 16 and the Comparative Tests show that hydrobromic acid is able to increase the amount of t-butyl hydroperoxide which oxidises the alkane. The hydroperoxide is thus used more efficiently.

TABLE 3
EFFECT OF HYDROBROMIC ACID ADDITION

| Example | Additive | % TBHP Consumed | % TBHP Selectivity | Mole % Product Distribution | | |
|---|---|---|---|---|---|---|
| | | | | Cyclohexanone | Cyclohexanol | t-Butyl cyclohexylperoxide |
| 17 | — | 100 | 51 | 40 | 27 | 35 |
| 18 | NaBr | 100 | 50 | 36 | 32 | 32 |
| 15 | HBr | 100 | 61 | 34 | 19 | 47 |
| 16 | HBr | 100 | 61 | 40 | 26 | 34 |
| 19 | HCl | 100 | 51 | 35 | 21 | 44 |
| 20 | HI | 100 | 30 | 45 | 36 | 19 |

We claim:

1. A process for the production of an alcohol, ketone or mixture thereof by oxidation of a corresponding alkane or alkene having from 3 to 20 carbon atoms which process comprises reacting the alkane or the alkene in the liquid phase at a temperature in the range ambient temperature to 140° C. with a hydrocarbyl hydroperoxide and an effective amount of a soluble ruthenium catalyst,
   wherein the reaction is carried out in the presence of hydrobromic acid or hydrogen bromide.

2. A process as claimed in claim 1 wherein the hydrocarbyl hydroperoxide is selected from an alky, cycloalkyl or aryl hydroperoxide.

3. A process as claimed in claim 2 wherein the hydrocarbyl hydroperoxide is selected from t- butylhydroperoxide, cumene hydroperoxide and cyclohexylhydroperoxide.

4. A process as claimed in claim 1 wherein the hydrobomic acid or hydrogen bromide is added in an amount which is less than 2% by weight of the reactants.

5. A process as claimed in claim 1 wherein the reaction is carried out in the presence of an inert solvent.

6. A process as claimed in claim 4 wherein the inert solvent is tertiary butanol.

7. A process as claimed in claim 1 wherein the soluble ruthenium catalyst is ruthenium trichloride or tris(acetoacetonate) ruthenium (III).

8. A process as claimed in claim 1 wherein the soluble ruthenium catalyst is a ruthenium porphyrin or a ruthenium phthalocyanine.

* * * * *